United States Patent [19]
Godfrey et al.

[11] Patent Number: 5,303,722
[45] Date of Patent: Apr. 19, 1994

[54] APPARATUS FOR BLEACHING HAIR UNDER THE INFLUENCE OF LIGHT

[75] Inventors: Robin E. Godfrey, Welwyn, Great Britain; Thomas Clausen; Wolfgang R. Balzer, both of Alsbach, Fed. Rep. of Germany

[73] Assignee: Wella Aktiengesellschaft, Darmstadt, Fed. Rep. of Germany

[21] Appl. No.: 1,799

[22] Filed: Jan. 8, 1993

Related U.S. Application Data

[62] Division of Ser. No. 691,051, Jun. 24, 1991, Pat. No. 5,246,019.

[30] Foreign Application Priority Data

Jan. 11, 1989 [GB] United Kingdom ............... 89245815

[51] Int. Cl.⁵ .......................................... A45D 24/00
[52] U.S. Cl. .................................. 132/219; 132/212; 15/105; 362/32; 362/109
[58] Field of Search ............... 132/102, 148, 208, 212, 132/219; 8/103, 115.52, 115.53, 127.51, 405, 428, 429; 433/29; 362/32, 109, 115, 253; 15/105, 167.1

[56] References Cited

U.S. PATENT DOCUMENTS

| | | | |
|---|---|---|---|
| 1,259,169 | 3/1918 | Train | 362/115 |
| 2,397,757 | 4/1946 | Schwedensky | 362/109 |
| 2,688,971 | 9/1954 | Daniels et al. | 362/115 |
| 3,261,978 | 7/1966 | Brenman | 15/167.1 |
| 3,289,679 | 12/1966 | Zellerman | 132/208 |
| 4,253,212 | 3/1981 | Fujita | 15/167.1 |
| 4,779,173 | 10/1988 | Carr et al. | 362/109 |
| 4,792,341 | 12/1988 | Kozikowski et al. | 8/103 |
| 5,030,090 | 7/1991 | Maeda et al. | 433/29 |
| 5,160,194 | 11/1992 | Feldman | 362/109 |

FOREIGN PATENT DOCUMENTS

| | | | |
|---|---|---|---|
| 0392951 | 10/1990 | European Pat. Off. | 433/29 |
| 9011728 | 10/1990 | PCT Int'l Appl. | 433/216 |

Primary Examiner—Gene Mancene
Assistant Examiner—Frank A. LaViola
Attorney, Agent, or Firm—Michael J. Striker

[57] ABSTRACT

The apparatus for bleaching hair has a light comb with a comb back, a plurality of comb teeth extending from the comb back, a device for guiding light from a light source through the comb back into the comb teeth, and a device for radiating the light from the comb teeth and parallel to the comb back, this radiating device receiving the light from the light guiding device.

11 Claims, 3 Drawing Sheets

APPARATUS FOR BLEACHING HAIR UNDER THE INFLUENCE OF LIGHT

This is a division of application Ser. No. 691,051, filed Jun. 24, 1991, now U.S. Pat. No. 5,246,019.

BACKGROUND OF THE INVENTION

The subject matter of the present invention is a process for bleaching hair in which the hair, which is treated beforehand with a composition containing an optical photosensitizer, is bleached under the influence of light, as well as means for bleaching hair under the influence of light.

As has already been known for a long time, human hair is bleached by sunlight. The degree to which the hair can be brightened depends on the original hair color and on the duration over which the sunlight is active.

However, since several days can pass before a visible bleaching effect is achieved by sunlight, even during intensive sun radiation, this method is not suitable for the intended bleaching.

A method for bleaching hair is known from U.S. Pat. No. 4,792,341 in which the hair is exposed to one or more radiation shocks of artificial light, wherein the light energy is sufficient for bleaching the melanin in the hair. The method known from the U.S. Pat. No. 4,792,341 is based on the thermal decomposition of melanin caused by the use of longwave radiation at high intensity. The intensity of the radiation striking the hair must be selected so as to be very high in this method, and an intensive heating of the hair is observed, so that the hair can be damaged.

At present the bleaching of hair is usually effected by means of the action of a bleaching agent on hair which contains an oxidizing agent, particularly hydrogen peroxide, wherein the bleaching action can be increased by means of the addition of salts of peracids.

The bleaching of hair which is used to change the natural hair color shade in a fashionable manner is chemically based on a change, e.g. an oxidative change, in the hair pigment melanin.

Although the melanin in the hair is present only in relatively small amounts, it is necessary to work with a large excess of hydrogen peroxide in the alkaline pH range when bleaching the hair with conventional bleaching agents containing hydrogen peroxide in order to ensure a sufficient bleaching effect.

In this currently conventional method for bleaching hair, hair damage cannot be avoided due to the excess of hydrogen peroxide used and the alkaline pH value.

The problem exists of providing a possibility for achieving a gentler bleaching of hair with light. A new method should be based on photochemical and not on photothermal reactions in order to prevent a heating of the hair which can damage the hair, as happens in the method known from U.S. Pat. No. 4,792,341. In addition, the new method should be capable of bleaching the hair without an excess of oxidizing agents within a suitable period of time by means of the photochemical production of a concentration of oxidizing agent adapted to the melanin concentration in the hair.

SUMMARY OF THE INVENTION

It has now been found that this problem has been solved in an outstanding manner by a process for bleaching hair under the influence of light in which a) first, a sufficient quantity, preferably 10 to 120 g, of a composition in the form of a solution, an emulsion or a gel containing at least one optical photosensitizer and a compound capable of providing a hydrogen radical is applied to the hair and allowed to act for up to 60 minutes, preferably 5 to 30 minutes, b) then, the hair is irradiated with visible light and/or ultraviolet light of a wavelength or wavelength range capable of activating the contained optical photosensitizer at an intensity sufficient for bleaching the hair, c) the hair is subsequently rinsed thoroughly and then dried.

The new method for bleaching hair is particularly gentle to the hair, since it is capable of achieving a good bleaching action, without the use of excesses of hydrogen peroxide, because of the in situ production of hydrogen peroxide in the hair. In addition, the bleaching process can be terminated immediately when the desired degree of brightening is achieved, since the light source can be switched off at any time. The desired degree of brightening can be controlled substantially better than in the previously conventional method for bleaching the hair with the use of compositions containing hydrogen peroxide by the new method for bleaching hair.

The in situ production of hydrogen peroxide is made possible by the optical photosensitizer which penetrates into the hair and produces a quantity of hydrogen peroxide sufficient for bleaching the melanin during irradiation with light with atmospheric oxygen and a compound capable of providing a hydrogen radical, particularly water or an alcohol.

In contrast to the photothermal process for bleaching hair known from U.S. Pat. No. 4,792,341, which leads to an intensive heating of the hair and resulting damage to the hair, the method according to the invention is based on the photochemical activation of an optical photosensitizer applied to the hair prior to irradiation and on the production of hydrogen peroxide in the hair which is effected by the latter. The light intensities used in the method, according to the invention, are therefore considerably lower. In addition, the irradiation of the hair is preferably effected in the continuous mode.

The amount of composition containing at least one optical photosensitizer which is applied in the first process step of the process, according to the invention, is particularly preferably 15 to 40 g, when the composition is in the form of a solution and particularly preferably 40 to 80 g when the composition is in the form of an emulsion or a gel.

In a special embodiment of the process, according to the invention, the hair is moistened with water prior to application of the composition containing the optical photosensitizer.

The subject matter of the present invention is further a composition for bleaching the hair under the influence of light for use according to the process, described above, in the form of a solution, an emulsion or a gel containing at least one compound capable of providing a hydrogen radical, characterized in that it contains at least one optical photosensitizer.

The composition according to the invention preferably contains 0.1 to 10 percent by weight, particularly preferably 0.5 to 5 percent by weight, of at least one optical photosensitizer.

The optical photosensitizer contained in the composition, according to the invention, is preferably a nonionic molecule which, as a result of its small size, is capable of penetrating into the hair and can be easily rinsed out again after bleaching.

The optical photosensitizer contained in the composition, according to the invention, should preferably be a triplet sensitizer, i.e. the molecular state of the optical photosensitizer activated by the light absorption is a triplet state whose energy is transmitted to an acceptor molecule without radiation. The optical photosensitizer which is excited in the triplet state can transmit its energy first to the acceptor molecule oxygen from which hydrogen peroxide is formed by means of the formation of singlet oxygen and hydrogen abstraction. On the other hand, the optical photosensitizer excited in the triplet state can also abstract hydrogen from the solvent and cause the oxidation of the melanin of the hair by a mechanism, which has not yet been completely explained, in the course of which hydrogen peroxide is formed. The multitude of chemical reactions which can be significant in such photo-oxidations are described e.g. in C.S. Foote, Science (1968), vol. 162. pages 963 to 970.

The importance of the two concurrent reaction mechanisms of the optical photosensitizer for the method described here for bleaching hair under the influence of light depends on the respective reaction conditions. The excited triplet state of the optical photosensitizer should be formed with a higher quantum yield and possess sufficient energy as well as a sufficient lifetime in order to ensure the formation of hydrogen peroxide in the hair by means of the reaction with oxygen of the air or a suitable solvent.

The composition, according to the invention, for bleaching the hair under the influence of light should preferably contain an optical photosensitizer which can be activated by visible light and/or ultraviolet light, but particularly preferably visible light.

The optical photosensitizer contained in the described composition, according to the invention, for bleaching the hair under the influence of light is preferably a ketone and can be selected e.g. from benzophenone, 3-bromobenzophenone, 4-bromobenzophenone, 2,2,4,4'-tetrahydroxybenzophenone, 2,5-dihydroxyacetophenone, benzil, p-benzoquinone, 2,3-butanedione, Michler's ketone, acetophenone, 4-benzoylbenzoic acid, methoxyacetophenone and 9-fluorenone.

Of the optical photosensitizers mentioned above, the composition, according to the invention, for bleaching hair under the influence of light preferably contains benzophenone.

The compound contained in the described composition for bleaching hair, which composition is capable of providing a hydrogen radical, can be e.g. water, but is preferably an alcohol, e.g. ethanol, methanol, isopropanol, cyclopentanol, benzyl alcohol, cyclohexanol or glycol. It is preferably contained in a quantity of 0.1 percent by weight.

The form of the composition, according to the invention, for bleaching hair under the influence of light is preferably a solution, particularly an alcoholic or aqueous-alcoholic solution. However, the form can also be a cream, a gel or an emulsion. The composition can also be sprayed in a mixture with a propellant gas or by a pump.

In addition to solvents like water and lower aliphatic alcohols, e.g. ethanol, propanol and isopropanol or glycols such as glycerin and 1,2-propylene glycol, conventional additions in solutions, creams, emulsions or gels are also wetting agents or emulsifiers from the classes of anionic, cationic, amphoteric or nonionogenic surface-active substances such as fatty alcohol sulfates, alkylbenzenesulfonates, alkyltrimethylammonium salts, alkyl betaines, ethoxylated fatty alcohols, ethoxylated nonylphenoles, fatty acid alkanol amides, ethoxylated fatty acid esters, as well as thickeners such as higher fatty alcohols, starches or cellulose derivatives, petrolatum, paraffin oil and fatty acids as well as grooming materials such as cationic resins, lanolin derivatives, cholesterin, pantothenic acid and betaine. The aforementioned ingredients are used in the usual quantities for such purposes, e.g. the wetting agents and emulsifiers in concentrations of approximately 0.5 to 30 percent by weight, the thickeners in a quantity of approximately 0.1 to 25 percent by weight and the grooming materials in a concentration of approximately 0.1 to 5.0 percent by weight.

The composition, according to the invention, must be free of the radical interceptors conventionally contained in cosmetics, such as tocopherol and ascorbic acid or its fatty acid esters or $\beta$-carotin and the ultraviolet filter substances conventionally contained in cosmetics insofar as these are not suitable as optical photosensitizers for the method according to the invention.

The light source which can be used in the second process step of the previously described process, according to the invention, should radiate light of a wavelength or wavelength range of visible light and/or of ultraviolet light which can activate the optical photosensitizers contained in the previously described composition for bleaching hair according to the invention.

In the second process step of the previously described process for bleaching hair, according to the invention, the hair is preferably irradiated by light of a light source selected from arc lamps, a deuterium lamp, a mercury discharge lamp or xenon lamp and lasers such as e.g. a semiconductor laser, a nitrogen laser or a helium-cadmium laser, but other light sources, e.g. the sun, are also suitable for the method, according to the invention, insofar as they can radiate the wavelength or wavelength range suitable for activating the respective optical photosensitizers at a sufficient intensity.

If light from an artificial light source is used for irradiation in process step (b) of the process according to the invention, which was described above, this is preferably operated in the continuous mode.

In process step (b) of the process according to the invention, the light of a suitable light source can be fed into a light comb which radiates light at the insides of the comb teeth, e.g. by means of optical fibers.

The light source used in process step (b) can also be arranged inside a hood which is opaque to ultraviolet light, which hood is placed over the hair similar to the hood of a drier, but, in contrast to the conventional drier hood, ends at its edge in such a way, e.g. in the form of a sleeve, that it prevents the light from exiting. The hood, which is opaque to ultraviolet light and is preferably vapor-plated at the inside, can also be equipped with a blower for removing heat and/or for moving the hair and/or for drying the hair. The hair should be irradiated in process step (b) of the process, according to the invention, which is described above, with visible and/or ultraviolet light whose intensity on the hair would not be sufficient for bleaching the hair within the irradiation period in question without the use of the optical photosensitizer. The irradiation period required for the bleaching of hair according to the process described above also depends, aside from other factors, e.g. the desired degree of brightening, on the type of light source as well as on the irradiation intensity (W/cm$^2$). The irradiation period in the process, according to the invention, is between 1 second, when using the light comb, and 2 days when sunlight is used for irradiation in process step (b), but the irradiation period is preferably 10 to 120 minutes.

If the desire degree of brightening is achieved by treating the hair according to the process, according to the invention, the hair can possibly be treated, before the composition containing the optical photosensitizers is rinsed out, with a post-treatment composition containing a material which is capable of deactivating the optical photosensitizer. This material can be a triplet quencher, e.g. $\beta$-carotin, which deactivates the excited triplet state of the optical photosensitizer. However, a material can also be used in the post-treatment composition, which material chemically changes the optical photosensitizer in such a way that the latter is no longer effective for the process, according to the invention, for bleaching hair under the influence of light.

A liquid in which the optical photosensitizer is soluble is used for rinsing out the hair in process step (c). Ethanol or an aqueous-alcoholic solution is preferably used in the case of benzophenone. The removal or deactivation of the optical photosensitizer should rule out a possible further bleaching of the hair by natural or artificial light sources, e.g. the sun or a sun lamp.

The process, according to the invention, is suitable for bleaching all human hair on the head. However, it can also be used for bleaching hair strands, hair parts and wigs as well as for bleaching animal hair, e.g. hides.

The process, according to the invention, for bleaching hair is particularly suited for producing brighter strands in the hair.

Brighter strands can be worked into the hair according to the process, according to the invention, e.g. with the use of strand foil hoods.

In a special embodiment form of the process, according to the invention, the hair is covered with a strand foil hood, which is known per se and is preferably selected in such a way that it is opaque or hardly pervious to ultraviolet light. The hood is then repeatedly penetrated by a, preferably thin, hook needle. The strands of hair arranged underneath are grasped and pulled out through the foil. A quantity of the composition, according to the invention, sufficient for saturation, a total of 50 to 100 g depending on the length of the hair, is applied to the strands of hair. After acting for a period of up to 60 minutes, preferably 5 to 30 minutes, the pulled out strands are irradiated with light of a wavelength or wavelength range capable of activating the optical photosensitizers contained in the composition, according to the invention, with an intensity sufficient for bleaching the hair. The strand foil hood is then removed, the hair is rinsed with a solvent suitable for dissolving the optical photosensitizer and then dried.

In another embodiment of the process according to the invention, the hair, which is possibly moistened with water, is first saturated with a quantity of the composition, according to the invention, sufficient for saturation, 10 to 120 g depending on the length of the hair, then covered with a strand foil hood which is opaque to ultraviolet light. The hood is then repeatedly penetrated by a preferably thin hook needle. The strands of hair arranged underneath are grasped and pulled out through the foil, and the pulled out strands are then irradiated with light of a wavelength or wavelength range capable of activating the optical photosensitizers contained in the composition, according to the invention, with an intensity sufficient for bleaching the hair. The strand foil hood is then removed, the hair is thoroughly rinsed with a solvent suitable for dissolving the optical photosensitizer, and dried.

The use of a strand foil hood which is opaque to ultraviolet light, particularly whose surface reflects radiation, offers the possibility of protecting the scalp from the effect of light. The reflecting surface reduces the heating of the strand foil hood and the light losses.

In another embodiment of the process, according to the invention, the hair, which may be moistened with water, is covered with a, e.g. vapor-plated, strand foil hood which is opaque or hardly pervious to ultraviolet light. The hood is then repeatedly penetrated by a preferably thin hook needle. The strands of hair arranged underneath are grasped and pulled out through the foil. A quantity of the composition, according to the invention, sufficient for saturation, a total of 50 to 100 g depending on the length of the hair, is applied to the strands of hair. After acting for a period of up to 60 minutes, preferably 5 to 30 minutes, a hood is placed over the head, which hood is opaque to ultraviolet light and in which a light source which radiates light of a wavelength or wavelength range capable of activating the optical photosensitizers contained in the composition, according to the invention, is arranged in such a way that a uniform irradiation of the hair strands is ensured. The pulled out strands are then irradiated with a light intensity sufficient for bleaching the hair.

The hood containing the light source and the strand foil hood, which is opaque to ultraviolet light, are then removed, the hair is rinsed with a solvent suitable for dissolving the optical photosensitizer and then dried.

In a special embodiment of the process, according to the invention, the hair, which is possibly moistened with water, is first saturated with a quantity of the composition, according to the invention, sufficient for saturation, 10 to 120 g depending on the length of the hair, then covered with a, e.g. vapor-plated, strand foil hood which is opaque or hardly pervious to ultraviolet light. The hood is then repeatedly penetrated by a preferably thin hook needle. The strands of hair arranged underneath are grasped and pulled out through the foil. A hood is then placed over the head, which hood is opaque to ultraviolet light and in which a light source which radiates light of a wavelength or wavelength range capable of activating the optical photosensitizers contained in the composition, according to the invention, is arranged in such a way that a uniform irradiation of the hair strands is ensured. The hair is then irradiated with a light intensity sufficient for bleaching the hair. The hood containing the light source and the strand foil hood, which is opaque to ultraviolet light, are then removed, the hair is rinsed with a solvent suitable for dissolving the optical photosensitizer and then dried.

In the process, according to the invention, it is possible for the hair to be washed prior to drying. Further, it is possible to rinse only the strands of hair with the solvent prior to removing the foil strand hood, insofar as only the pulled out strands are saturated with the optical photosensitizers.

The bleaching of the hair can also be effected with a light comb. In this embodiment form of the process, according to the invention, a light comb is used in process step (b) as an irradiation source, which light comb radiates light only at the insides of the comb teeth and in which the light to be emitted is supplied by a suitable light source, e.g. of optical fibers.

The subject matter of the present invention is additionally an apparatus for bleaching the hair under the influence of light which is provided as a light comb whose light is emitted between the comb teeth parallel to the back of the comb or toward the back of the comb.

As a result of the emission of light between the comb teeth and parallel to the back of the comb or toward the back of the comb, the hair to be bleached which is located between the teeth of the comb is selectively irradiated, and not the scalp.

In the light comb, according to the invention, the radiating directions of the light should preferably lie in the plane in which the comb teeth and the back of the comb extend. The light comb, according to the invention, can have a plurality of light outlets which are substantially provided between adjacent comb teeth.

Flexible light guides, which can be optical fibers, are provided in an embodiment example of the light comb, according to the invention. A flexible sleeve for receiving a fiber-optic cable is provided at the light comb. On the one hand, this sleeve protects the optical fibers supported in it and, on the other hand, simplifies the handling of the light comb. The flexible light guide can also be constructed as a flexible tube which is filled with a liquid suitable for conducting light.

The distribution of the light entering into the light comb, according to the invention, on the individual comb teeth can be effected in such a way that the light intensity present in every intermediate space between the teeth of the comb is identical. This can be effected by uniform distribution of the light on the individual teeth by optical fibers. In an advantageous manner, the uniform distribution of light can also be effected by partially permeable mirrors. Corresponding exemplary embodiment of the light distribution within the comb are shown in the following in example B.

EXAMPLE

Process for Bleaching Hair

A strand of medium-blond human hair is suspended vertically in a quartz vessel which is filled with the following solution until the tips of the hair dip into the solution:

3 g benzophenone
97 g ethanol (99.7%)
―――――
100 g

The light of a 150 W xenon low-pressure arc lamp (model C 9515 by Cathodean, Cambridge) is focussed on the hair strand. The hair strand is irradiated for 1 hour with a light intensity of 4 W cm$^{-2}$ and a wavelength range of 300 to 850 nm. The hair strand is then removed from the tank, rinsed with ethanol and dried. The strand of hair which was originally medium-blond is bleached bright blond.

BRIEF DESCRIPTION OF THE DRAWING

The light comb is described in more detail in the following with reference to figures showing an embodiment example.

DETAILED DESCRIPTION OF A PREFERRED EMBODIMENT

Figure 1:
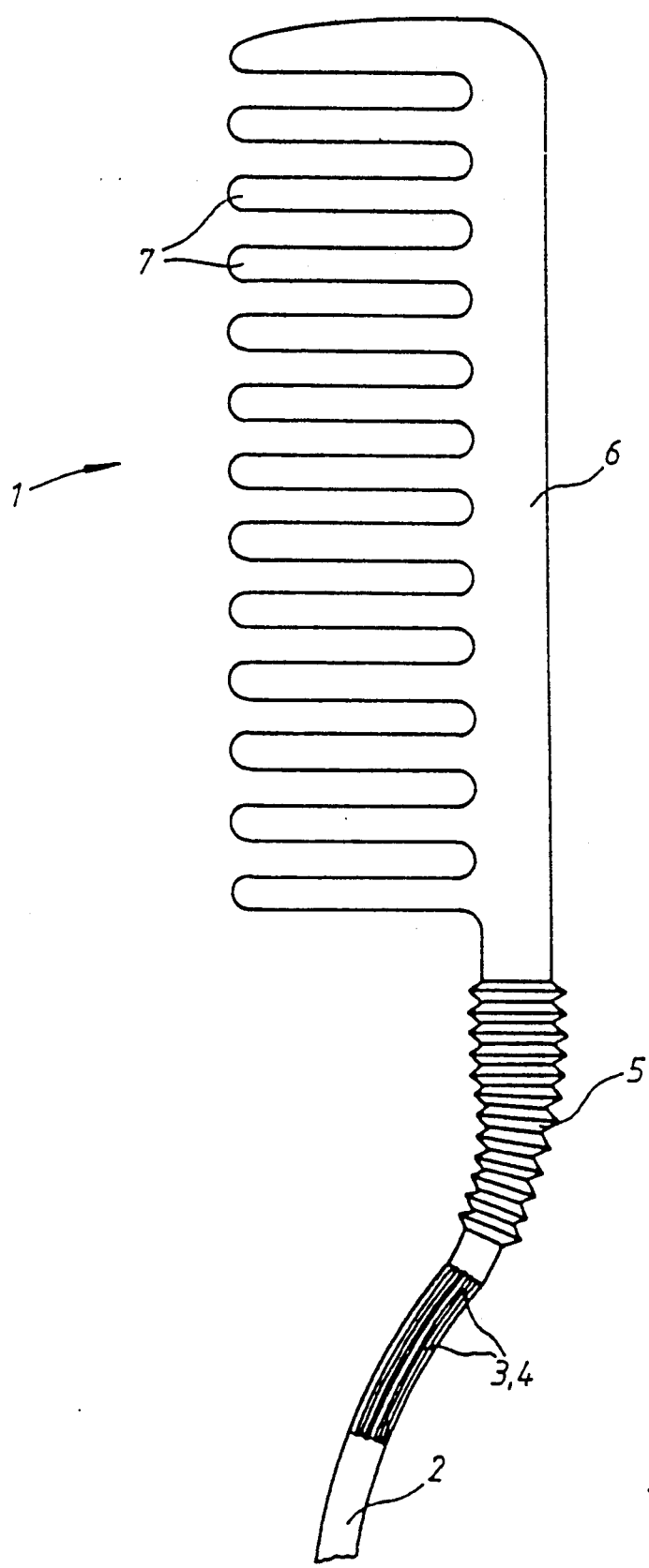
FIG. 1 is a side view with partial vertical section through a light comb which is provided with light by a fiber-optic cable.

The light comb 1 substantially has the form of a hair comb (FIG. 1). It is provided with light from a light source, not shown, via a fiber-optic cable 2. The fiber-optic cable 2 contains individual optical fibers 4 as light guides which are guided through a flexible sleeve 5 into the hollow back 6 of the comb and are then distributed on the hollow comb teeth 7.

Figure 2:
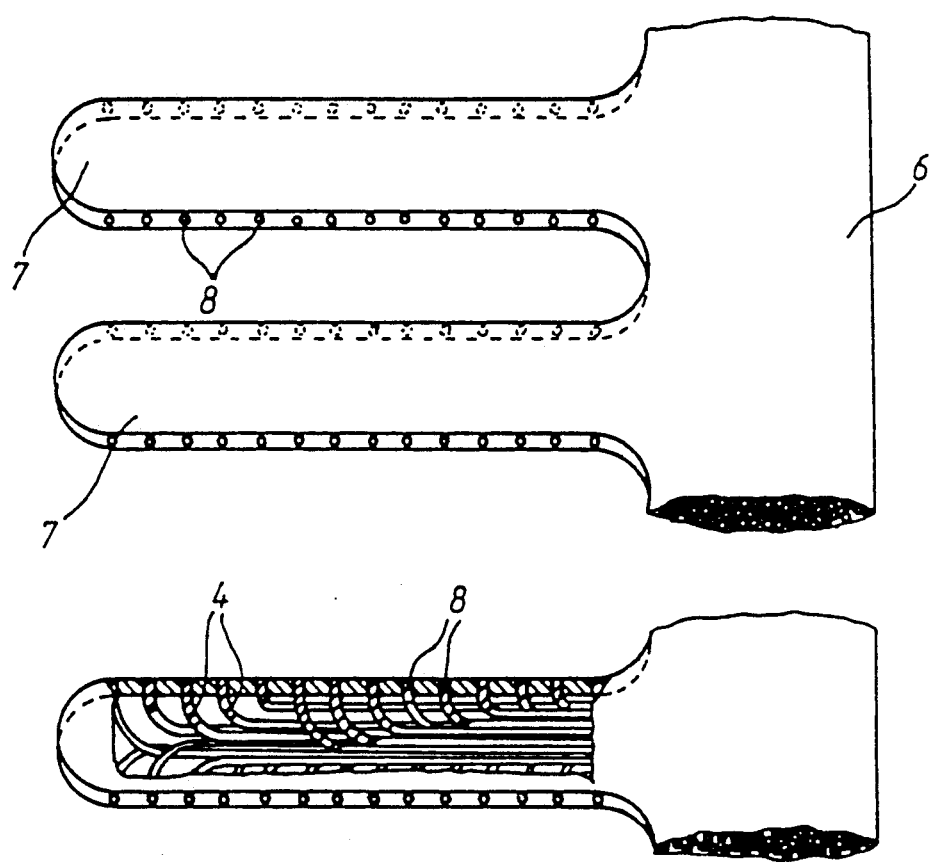
FIG. 2 is partially a perspective, partially a cross-sectional view through a part of the light comb according to FIG. 1 with light outlets which are arranged linearly at the comb teeth and individual optical fibers opening into the latter.

The optical fibers 4 open into light outlets 8 which are arranged in straight-line rows at the comb teeth 7 in such a way (FIG. 2) that the light is radiated in the plane in which the light comb 1 extends only parallel to the back 6 of the comb in order to irradiate only the hair itself as much as possible during a hair treatment.

Figure 3:
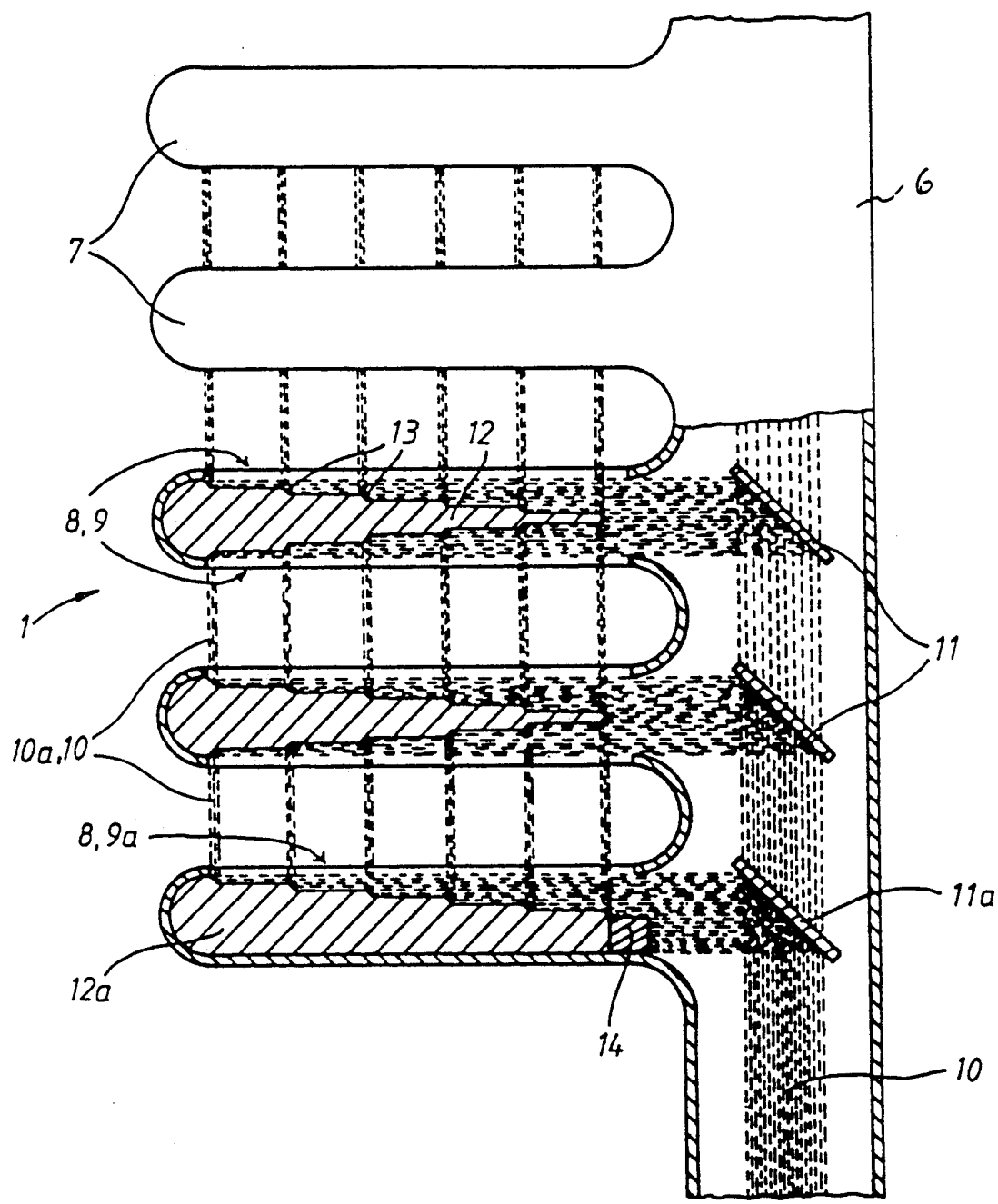
FIG. 3 is partially a side view, partially a cross-sectional view through another embodiment example of a light comb, partially permeable mirrors being arranged one after the other in the hollow back of the comb in order to guide light into individual light outlet gaps via reflectors.

FIG. 3 shows a light comb 1 in which light outlet gaps 9 are provided as light outlets 8. The light 10 from the flexible light guide 3 is guided into the light outlet gaps 9 by means of partially permeable mirrors 11 and reflectors 12. In order to distribute the entire light output to the individual light outlet gaps in uniform proportions, the respective light permeability of a mirror 11 is selected in such a way that, with a total of n mirrors, it guides the nth part of the radiated light output to the light outlet gap 9a adjacent to it or the two light gaps 9 adjacent to it. This is the case when the nth mirror 11, as counted from the flexible light guide 3, with a total of x mirrors 11, has a light permeability of $$\frac{x - n}{x - (n - 1)}.$$

Reflectors 12 with steplike surfaces deflect the light at an angle of 90°, so that light is radiated between the comb teeth only parallel to the back 6 of the comb.

As a result of the reduction of surfaces 13 actually reflecting at the reflector 12, which surfaces 13 are arranged at a 45° angle relative to the incident light beam, their quantity on the reflector 12 can be increased. Accordingly, the quantity of beam bundles 10a is likewise increased and a virtually uniform light radiation is achieved between the comb teeth 7. Half of the light diaphraghmed out by the first mirror 11a is beamed on a light absorber 14 and transformed into heat. This amount of heat is relatively small.

Instead of the described reflectors 12, other reflectors, e.g. concave mirrors, can also be inserted in the comb teeth. A concave mirror inserted into the tip of a comb tooth 7 can irradiate the intermediate space between two comb teeth 7 in a particularly uniform manner. The radiated angular area then extends from a straight line extending through the tips of the comb teeth 7 until the edge lines of the gaps 9, 9a.

While the invention has been illustrated and described as embodied in a composition, means and process for bleaching hair under the influence of light, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

1. Apparatus for bleaching hair with light, comprising a light comb having a comb back, a plurality of comb teeth extending from said comb back, means for guiding light from a light source through said comb back into said comb teeth, and means for radiating said light from said comb teeth and parallel to said comb back, said means for radiating said light receiving said light from said means for guiding and being positioned within said comb teeth so as to allow for uniform irradiation of all portions of said hair.

2. Apparatus for bleaching hair with light according to claim 1, wherein said comb teeth and said comb back extend in a plane and said light is radiated in said plane in which said comb teeth and said comb back extend by said means for radiating.

3. Apparatus for bleaching hair with light according to claim 2, wherein said means for radiating said light includes a plurality of light outlets provided in at least one of said comb teeth and arranged substantially linearly along said least one of said comb teeth.

4. Apparatus for bleaching hair with light according to claim 1, wherein said means for guiding said light includes flexible light guides.

5. Apparatus for bleaching hair with light according to claim 4, wherein the flexible light guides are optical fibers.

6. Apparatus for bleaching hair with light according to claim 5, wherein said means for radiating includes a plurality of light outlets provided in each of said comb teeth, said light outlets being arranged substantially linearly along each of said comb teeth, and wherein each of said optical fibers opens into one of said light outlets.

7. Apparatus for bleaching hair with light according to claim 5, wherein said means for guiding includes a flexible sleeve and a fiber-optic cable containing said optical fibers, said flexible sleeve being positioned to receive said fiber-optic cable and connected to said comb back so that said optical fibers pass through said flexible sleeve into said comb back.

8. Apparatus for bleaching hair with light, comprising a light comb having a comb back, a plurality of comb teeth extending from said comb back, means for guiding light from a light source through said comb back into said comb teeth, and means for radiating said light from said comb teeth and parallel to said comb back, said means for radiating including flexible light guides connected to said comb back and at least one light outlet gap provided in at least one of said comb teeth so as to allow for uniform irradiation of all portions of said hair.

9. Apparatus for bleaching hair with light according to claim 8, wherein said means for radiating includes a reflector in said at least one of said comb teeth having said at least one light outlet gap and said means for guiding includes a plurality of partially light permeable mirrors arranged in said comb back so that said light emitted from said flexible light guides is guided into each of said light outlet gaps via said reflectors by said partially light permeable mirrors.

10. Apparatus for bleaching hair with light according to claim 9, wherein said plurality of said partially light permeable mirrors and the nth of said partially light permeable mirrors, as counted from said flexible light guide.

$$\frac{x - n}{x - (n - 1)}.$$

11. Apparatus for bleaching a hair with light according to claim 9, further comprising a light absorber positioned to receive an excess light portion from said partially light permeable mirrors.

* * * * *